United States Patent
Chen et al.

(10) Patent No.: US 7,851,747 B2
(45) Date of Patent: Dec. 14, 2010

(54) ELECTRODE STRUCTURE FOR DRIFT TUBE IN ION MOBILITY SPECTROMETER

(75) Inventors: Zhiqiang Chen, Beijing (CN); Yuanjing Li, Beijing (CN); Hua Peng, Beijing (CN); Qingjun Zhang, Beijing (CN); Jin Lin, Beijing (CN); Shaoji Mao, Beijing (CN); Zhude Dai, Beijing (CN); Shiping Cao, Beijing (CN); Zhongxia Zhang, Beijing (CN); Yangtian Zhang, Beijing (CN); Dexu Lin, Beijing (CN); Qinghua Wang, Beijing (CN); Shaofeng Wang, Beijing (CN); Hui Li, Beijing (CN)

(73) Assignees: Nuctech Company Limited (CN); Tsinghua University (CN)

( * ) Notice: Subject to any disclaimer, the term of this patent is extended or adjusted under 35 U.S.C. 154(b) by 16 days.

(21) Appl. No.: 12/455,029

(22) Filed: May 27, 2009

(65) Prior Publication Data

US 2009/0309013 A1 Dec. 17, 2009

(30) Foreign Application Priority Data

Jun. 12, 2008 (CN) .................. 2008 1 0114816

(51) Int. Cl.
*H01J 49/40* (2006.01)

(52) U.S. Cl. .................. 250/287; 250/281; 250/282; 250/288; 250/290; 250/292

(58) Field of Classification Search .................. 250/281, 250/282, 286, 287, 288, 290, 292
See application file for complete search history.

(56) References Cited

U.S. PATENT DOCUMENTS

| 4,390,784 | A | 6/1983 | Browning et al. |
| 5,280,175 | A | 1/1994 | Karl |
| 6,051,832 | A | 4/2000 | Bradshaw |
| 6,229,143 | B1 | 5/2001 | Wernlund |
| 6,897,437 | B2 * | 5/2005 | Fuhrer et al. .................. 250/287 |
| 7,164,122 | B2 * | 1/2007 | Fuhrer et al. .................. 250/287 |

* cited by examiner

*Primary Examiner*—Jack I Berman
*Assistant Examiner*—Michael Maskell
(74) *Attorney, Agent, or Firm*—Schwegman, Lundberg & Woessner, P.A.

(57) ABSTRACT

Disclosed is an electrode structure for a drift tube in IMS comprising a ring electrode, for each of two surfaces of the ring electrode, at least a part adjacent to the inner radius is formed into a cone, and the angles formed between the cones and the axis of the ring electrode are different from each other. The electrode structure of the present invention can alleviate, even eliminate, the accumulation of space charges in the drift tube. Such structure is particularly suitable when the electric field in the drift tube is low in strength or a great number of ions pass through. Meanwhile, the structure allows a significant decrease in the size of the outer radius of the electrode, while the inner radius remains constant. In this way, it is possible to effectively reduce the outline size of the drift tube and thus make the IMS compact.

3 Claims, 2 Drawing Sheets

ELECTRODE STRUCTURE FOR DRIFT TUBE IN ION MOBILITY SPECTROMETER

RELATED APPLICATION

This application claims the benefit of priority, under 35 U.S.C. Section 119, to Chinese Patent Application Serial No. 200810114816.1, filed on Jun. 12, 2008, which is incorporated herein by reference in its entirety.

BACKGROUND OF THE INVENTION

1. Field of Invention

The present invention relates to a detection system for ion mobility spectrometer (IMS) in a technical field of detecting explosives, drugs and the like. In particular, the present invention relates to an electrode structure for a drift tube in IMS.

2. Description of Prior Art

The drift tube in the conventional IMS is generally made of a series of electrode plates and insulators. When ions move in the drift tube, part of the ions which move near the electrodes will hit the insulators and generate space charges. The accumulated charges will affect the uniform electric field in the drift tube and cause abnormality of the IMS. Such situation becomes even more noticeable when the electric field in the drift tube is weak or a large number of ions are collected together (e.g., the drift tube has gotten poisoned).

To avoid the occurrence of the above situation, the inner radius of an electrode is generally made smaller than that of an insulator during fabrication of an IMS. Unfortunately, this fabrication process reduces the effective usable size of the inner radius of the IMS, while its outline size becomes larger. So, limitation is imposed on the development of IMS products towards compactness, lightness and convenience.

In the past decades, the conventional IMS drift tube is mainly developed in consideration of how to form a uniform electric field (U.S. Pat. Nos. 6,229,143, 5,280,175), focusing (U.S. Pat. No. 7,164,122) and less cost (U.S. Pat. No. 6,051,832). No attempt is made to improve the drift tube with respect to the effect of charge accumulation. Only U.S. Pat. No. 4,390,784 describes a technique to eliminate the charge accumulation phenomenon in the drift tube.

U.S. 4,390,784 discloses that the accumulation of space charge in the drift tube can be abated by evaporation plating a resistance film in the glass tube, and it is also possible to reduce the outline size of the drift tube with its inner radius being the same as the conventional drift tube. This lays a foundation for the development of the IMS towards compactness.

In the drift tube using a resistance film, however, charges will hit onto the resistance film and cause a local potential change within the drift tube. This will increase the FWHM of detected spectrum and reduce the resolution of the IMS. Further, the method loses the ability to focus ions and requires a high production cost, when compared with the conventional drift tube using electrode rings.

FIG. 1 is a schematic diagram of a conventional drift tube using electrode rings. As shown in FIG. 1, to prevent ions from hitting onto the insulator and causing charge accumulation, the conventional drift tube has an inner radius of the electrode rings smaller than that of the insulator. As such, a channel is formed between two electrode rings, and most of the ions will hit onto the rings, instead of passing through the channel to hit the insulator. With such configuration, the outer radius of the drift tube becomes generally large.

SUMMARY OF THE INVENTION

In view of the above disadvantages of the conventional IMS, the present invention provides a novel electrode structure for a drift tube in IMS, which can alleviate, even eliminate, the accumulation of space charge in the drift tube while reducing space dead zone. Meanwhile, the electrode structure can efficiently reduce the outline size of the drift tube with the inner radius being unchanged, and thus reduce the volume of the IMS product.

In an aspect of the present invention, an electrode structure for a drift tube in IMS is provided comprising at least one ring electrode, for each of two surfaces of each ring electrode, at least a part adjacent to the inner radius is formed into a cone, and the angles formed between the cones and the axis of the ring electrode are different from each other.

Preferably, a first angle between the cone at the upstream in the direction of ion movement and the axis of the ring electrode is larger than a second angle between the cone at the downstream in the direction of ion movement and the axis of the ring electrode.

Preferably, the ring electrode has a smaller thickness on the outer radius than on the inner radius.

The electrode structure of the present invention can alleviate, even eliminate, the accumulation of space charges in the drift tube. Such structure is particularly suitable when the electric field in the drift tube is weak or a great number of ions transmitting. Meanwhile, the structure allows a significant decrease in the size of the outer radius of the electrode, while the inner radius remains constant. In this way, it is possible to effectively reduce the outline size of the drift tube and thus make the IMS compact.

BRIEF DESCRIPTION OF THE DRAWINGS

The above advantages and features of the present invention will be apparent from the following detailed description on the preferred embodiments taken conjunction with the drawings in which.

DETAILED DESCRIPTION OF THE PREFERRED EMBODIMENTS

Now, preferred embodiments of the present invention will be described with reference to the figures, in which the same reference symbol, though shown in different figures, denotes the same or like component.

Figure 1:
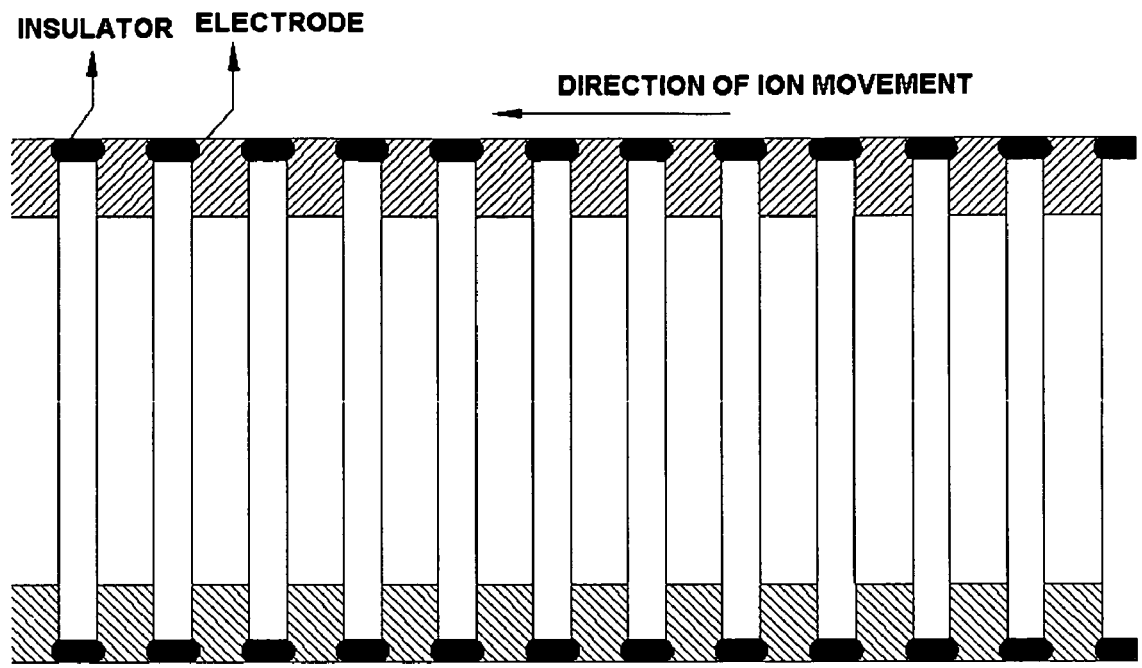
FIG. 1 is a schematic diagram of a drift tube using conventional electrodes.
Figure 2:
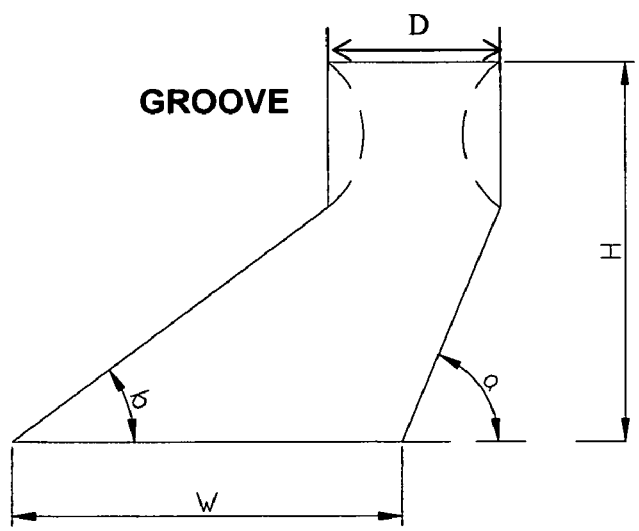
FIG. 2 is a schematic diagram showing part of the cross section of an electrode structure according to an embodiment of the present invention.

To effectively reduce the outline size of the IMS while keeping the same structure, an embodiment of the present invention provides an electrode ring structure. FIG. 2 is a schematic diagram showing part of the cross section of an electrode structure according to an embodiment of the present invention. The electrode structure of the present embodiment is provided with a ring electrode having a thickness. For each of two surfaces of the ring electrode, the part adjacent to the inner radius is fabricated into a cone. In other words, each of the surfaces of the ring electrode is partly cut into a cone on the side of the inner radius. Furthermore, the formed two cones have different angles with respect to the axis of the drift tube.

In general, ions move from right to left along the tube axis in FIG. 2. As shown in FIG. 2, the angles between the two cones and the axis of the drift tube are donated as a and b, respectively, and it is required that b<a. More specifically, the angle a between the cone at the upstream in the direction of ion movement and the axis of the ring electrode is greater than the angle b between the cone at the downstream in the direction of ion movement and the axis of the ring electrode.

In FIG. 2, the difference between the inner and outer radiuses of the ring electrode is denoted as H, the thickness on the inner radius of the electrodes is denoted as W, the thickness on the outer radius is denoted as D, and W>D. Grooves can be formed in the regions, which are closer to the outer radius, of the two surfaces of the ring electrode so as to fasten or seal insulators.

Figure 3:
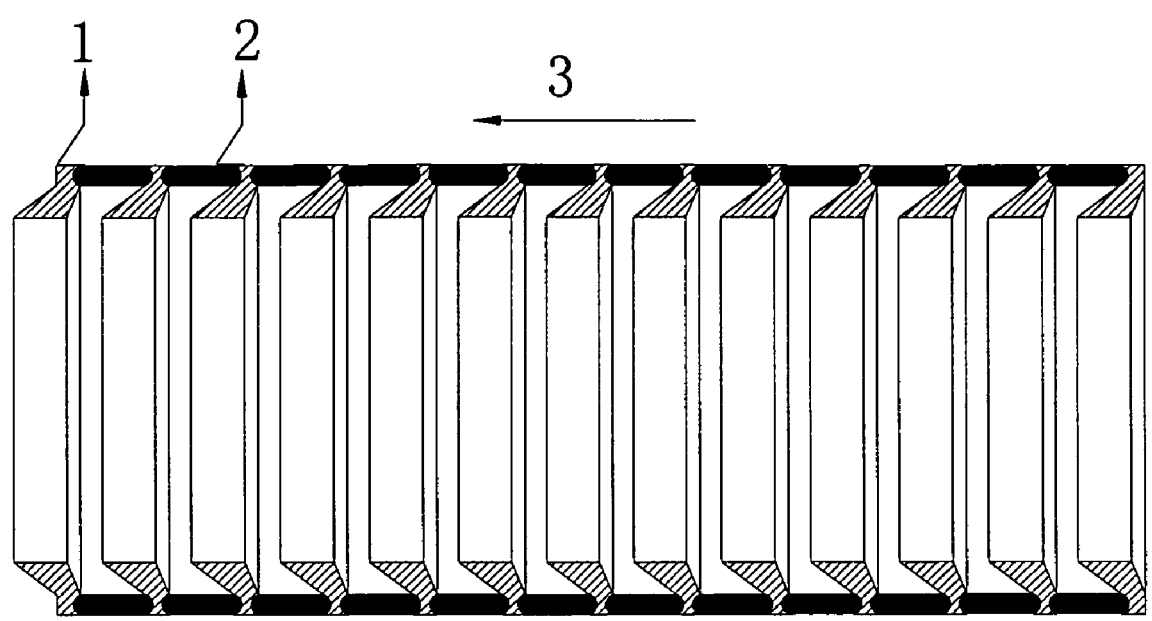
FIG. 3 is a schematic diagram of application of the drift tube according to an embodiment of the present invention.

As shown in FIG. 3, a plurality of electrode structures 1 and insulators 2 are alternately coupled to form a drift tube in IMS. Every two electrode structures are insulated from each other by one ring-shaped ceramic body which may be called insulator. The coned part of each ring electrode is tilted along the direction of ion movement 3, and thus a long channel is formed between every two ring electrodes. Since the angles a, b between the two surfaces of each ring electrode and the axis of the drift tube satisfy the relationship b<a, most of the insulators are screened by the electrodes. An approximately uniform electric field can be created along the axis of the tube in the drift tube by applying incrementing (decrementing) potential to the individual ring electrodes. Meanwhile, an electric field titled with respect to the axis of the tube can be generated on the coned portions of two adjacent ring electrodes. When sample ions drift along the axis of the tube towards the detector, part of the ions will enter the channel between two ring electrodes. Thanks to the long channel, most of the ions will hit onto the ring electrodes and get lost, rather than accumulating on the insulators and causing space charge. So, it is possible to shorten the outer radius of the ring electrode and thus to reduce the volume of the drift tube when the drift tube is long or the inner radius is constant. In other words, the ring electrode can have a small value of H, and it can benefit the construction of a compact IMS.

The foregoing description is only the preferred embodiments of the present invention and not intended to limit the present invention. Those ordinarily skilled in the art will appreciate that any modification or substitution in the principle of the present invention shall fall into the scope of the present invention defined by the appended claims.

What is claimed is:

1. An electrode structure for a drift tube in IMS comprising at least one ring electrode, for each of two surfaces of each ring electrode, at least a part adjacent to the inner radius is formed into a cone, and the angles formed between the cones and the axis of the ring electrode are different from each other.

2. The electrode structure of claim 1, wherein a first angle between the cone at the upstream in the direction of ion movement and the axis of the ring electrode is greater than a second angle between the cone at the downstream in the direction of ion movement and the axis of the ring electrode.

3. The electrode structure of claim 1, wherein the ring electrode has a smaller thickness on the outer radius than on the inner radius.

* * * * *